(12) United States Patent
Gross et al.

(10) Patent No.: US 9,283,132 B2
(45) Date of Patent: Mar. 15, 2016

(54) PATIENT POSITIONING APPARATUS AND A MEDICAL IMAGING APPARATUS COMPRISING THE PATIENT POSITIONING APPARATUS

(71) Applicants: Patrick Gross, Buckenhof (DE); Martin Ringholz, Erlangen (DE)

(72) Inventors: Patrick Gross, Buckenhof (DE); Martin Ringholz, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 263 days.

(21) Appl. No.: 13/958,917

(22) Filed: Aug. 5, 2013

(65) Prior Publication Data

US 2014/0048077 A1 Feb. 20, 2014

(30) Foreign Application Priority Data

Aug. 14, 2012 (DE) .......................... 10 2012 214 449

(51) Int. Cl.
*A61G 13/12* (2006.01)
*A61B 5/055* (2006.01)
*A61B 19/00* (2006.01)

(52) U.S. Cl.
CPC ............ *A61G 13/121* (2013.01); *A61B 5/0555* (2013.01); *A61B 19/203* (2013.01)

(58) Field of Classification Search
CPC .. A61B 6/0407; A61B 6/0442; A61B 6/0471; A61B 6/04; A61B 6/0421; A61B 19/203; A61B 5/0555; A61G 13/121; A61G 13/12; A61F 5/05883

USPC ............................................................ 403/62
See application file for complete search history.

(56) References Cited

U.S. PATENT DOCUMENTS

| | | | | |
|---|---|---|---|---|
| 3,188,079 A | * | 6/1965 | Boetcker et al. | 5/622 |
| 5,233,713 A | * | 8/1993 | Murphy et al. | 5/636 |
| 5,276,927 A | * | 1/1994 | Day | 5/622 |
| 5,509,747 A | * | 4/1996 | Kiendl | 403/102 |
| 5,564,663 A | * | 10/1996 | Cook et al. | 248/222.12 |
| 6,003,174 A | * | 12/1999 | Kantrowitz et al. | 5/601 |
| 6,199,233 B1 | * | 3/2001 | Kantrowitz et al. | 5/601 |
| 6,557,195 B2 | * | 5/2003 | Dinkler | 5/601 |
| 6,584,630 B1 | * | 7/2003 | Dinkler | 5/622 |
| 6,739,006 B2 | * | 5/2004 | Newkirk et al. | 5/622 |
| 6,813,788 B2 | * | 11/2004 | Dinkler et al. | 5/622 |
| 7,117,551 B1 | * | 10/2006 | Dinkler et al. | 5/637 |
| 7,544,007 B2 | * | 6/2009 | Easton | 403/322.4 |
| D603,967 S | * | 11/2009 | Berry et al. | D24/184 |
| 7,789,560 B2 | * | 9/2010 | Moyers | 378/205 |
| 7,882,583 B2 | * | 2/2011 | Skripps | 5/621 |
| 8,424,133 B1 | * | 4/2013 | Rossi et al. | 5/601 |
| 8,425,404 B2 | * | 4/2013 | Wilson et al. | 600/102 |
| 8,503,759 B2 | * | 8/2013 | Greer et al. | 382/153 |

(Continued)

FOREIGN PATENT DOCUMENTS

DE 19910289 A1 9/2000

*Primary Examiner* — David E Sosnowski
*Assistant Examiner* — Eric Kurilla

(57) ABSTRACT

A patient positioning apparatus is provided. The patient positioning apparatus includes a positioning table, a transfer plate, which is arranged on the positioning table so as to be moveable relative to the positioning table, and a positioning unit for a positioning of a surgical head securing unit on the transfer plate, wherein the positioning unit exhibits a joint unit with at least one first rotational joint unit, wherein the at least one first rotational joint unit exhibits a predetermined stop position for a rotational movement.

16 Claims, 3 Drawing Sheets

(56) References Cited

U.S. PATENT DOCUMENTS

| | | | |
|---|---|---|---|
| 8,806,679 B2 * | 8/2014 | Soto et al. | 5/600 |
| 8,893,333 B2 * | 11/2014 | Soto et al. | 5/640 |
| 2002/0032927 A1 * | 3/2002 | Dinkler | 5/601 |
| 2003/0084512 A1 * | 5/2003 | Fujita et al. | 5/601 |
| 2003/0145383 A1 | 8/2003 | Schwaegerle | |
| 2003/0152197 A1 * | 8/2003 | Moyers | 378/204 |
| 2004/0055089 A1 * | 3/2004 | Dinkler et al. | 5/622 |
| 2004/0243147 A1 * | 12/2004 | Lipow | 606/130 |
| 2005/0067875 A1 * | 3/2005 | DeBraal et al. | 297/409 |
| 2006/0190010 A1 * | 8/2006 | Easton | 606/130 |
| 2006/0290195 A1 * | 12/2006 | Roleder et al. | 297/900 |
| 2006/0293589 A1 * | 12/2006 | Calderon et al. | 600/415 |
| 2008/0072381 A1 * | 3/2008 | Rolfes et al. | 5/622 |
| 2008/0078031 A1 * | 4/2008 | Weinstein et al. | 5/630 |
| 2010/0071128 A1 * | 3/2010 | Campagna et al. | 5/81.1 R |
| 2010/0249575 A1 * | 9/2010 | Shvartsberg et al. | 600/415 |
| 2010/0249780 A1 * | 9/2010 | Rolfes | 606/59 |
| 2010/0296723 A1 * | 11/2010 | Greer et al. | 382/153 |
| 2010/0319706 A1 * | 12/2010 | Berry et al. | 128/845 |
| 2010/0329414 A1 * | 12/2010 | Zhu et al. | 378/4 |
| 2011/0188627 A1 * | 8/2011 | Ishii | 378/20 |
| 2012/0124742 A1 * | 5/2012 | Soto et al. | 5/600 |
| 2012/0124747 A1 * | 5/2012 | Soto et al. | 5/622 |
| 2012/0124748 A1 * | 5/2012 | Soto et al. | 5/640 |
| 2012/0260429 A1 * | 10/2012 | Rolfes | 5/637 |
| 2012/0260923 A1 * | 10/2012 | Campagna | 128/845 |
| 2012/0271142 A1 * | 10/2012 | Campagna | 600/407 |
| 2012/0278993 A1 * | 11/2012 | Gard et al. | 5/640 |
| 2012/0310078 A1 * | 12/2012 | Harder et al. | 600/410 |
| 2013/0023754 A1 * | 1/2013 | Harder et al. | 600/415 |
| 2013/0081636 A1 * | 4/2013 | Schuele | 128/845 |
| 2013/0190604 A1 * | 7/2013 | Moffatt | 600/411 |
| 2013/0219620 A1 * | 8/2013 | Eder et al. | 5/601 |
| 2013/0219621 A1 * | 8/2013 | Eder et al. | 5/601 |
| 2013/0298329 A1 * | 11/2013 | Eder et al. | 5/601 |
| 2013/0324834 A1 * | 12/2013 | Majewski et al. | 600/411 |
| 2013/0334439 A1 * | 12/2013 | Etters | 250/453.11 |
| 2014/0020180 A1 * | 1/2014 | Eder et al. | 5/601 |
| 2014/0024925 A1 * | 1/2014 | Piferi | 600/415 |
| 2014/0033437 A1 * | 2/2014 | Gross et al. | 5/622 |
| 2014/0053333 A1 * | 2/2014 | Krieg et al. | 5/601 |
| 2014/0059771 A1 * | 3/2014 | Schuele et al. | 5/622 |
| 2014/0116450 A1 * | 5/2014 | Li et al. | 128/876 |
| 2014/0221815 A1 * | 8/2014 | Aklan et al. | 600/411 |
| 2014/0245537 A1 * | 9/2014 | Allen | 5/622 |
| 2015/0045676 A1 * | 2/2015 | Dawson et al. | 600/476 |
| 2015/0112187 A1 * | 4/2015 | Petropoulos et al. | 600/422 |

* cited by examiner

PATIENT POSITIONING APPARATUS AND A MEDICAL IMAGING APPARATUS COMPRISING THE PATIENT POSITIONING APPARATUS

CROSS REFERENCE TO RELATED APPLICATIONS

The present application claims priority to German application No. 102012214449.8 DE filed Aug. 14, 2012, the entire content of which is hereby incorporated herein by reference.

FIELD OF INVENTION

The present invention relates to a patient positioning apparatus, comprising a positioning table, a transfer plate, which is arranged on the positioning table so as to be moveable relative to the positioning table, and a positioning unit for the positioning of a surgical head securing unit on the transfer plate.

BACKGROUND OF INVENTION

For neurosurgical interventions, the patient is positioned on a patient positioning apparatus, in particular an operating table apparatus. In this situation, the patient is positioned on a transfer plate, since a medical imaging examination, such as a magnetic resonance examination, of the head region of the patient is frequently carried out during an interruption in the neurosurgical intervention and/or after the termination of the neurosurgical intervention. In this situation, by means of the transfer plate, the patient is moved between the operating table and a further patient positioning apparatus, which is designed to be magnetic resonance-compatible for a magnetic resonance examination. For the neurosurgical intervention, a surgical head clamping unit is attached to the patient, in particular to the head of the patient, or the head of the patient is positioned inside this surgical head clamping unit, wherein the surgical head clamping unit is arranged, for example, on the transfer plate, and, together with the head of the patient, projects over the transfer plate.

For the surgical head clamping unit, there is a maximum permissible positioning range available, which, in particular, is dimensioned in accordance with a cross-sectional area of a patient accommodation area of the medical imaging apparatus. If the surgical head clamping unit projects beyond the positioning range which is permissible for the surgical head clamping unit, then, when the patient positioned on the transfer plate is introduced, together with the surgical head clamping unit, into the patient accommodation area, this can lead to undesirable collisions, in particular with a housing of the medical imaging apparatus. This increases the risk of injury to the patient. In addition to this, the surgical head clamping unit must be repositioned in order for it to be possible for a medical imaging examination to be carried out at all. This repositioning can lead to undesirable delays, since for the repositioning it is first necessary for a sterile covering of the surgical head clamping unit to be removed.

The positioning of the surgical head clamping unit and/or of the head of the patient is carried out by a surgeon and/or a clinical operating personnel, wherein this positioning is very complicated. As well as this, the positioning takes place on the basis of a rough assessment of the permissible positioning range and/or in accordance with empirical values from the surgeon and/or the operating personnel. This can however lead to situations in which, for example, only a fraction of the permissible positioning range is used, or, during the introduction into the medical imaging apparatus, collisions may occur.

SUMMARY OF INVENTION

The present invention is based in particular on the object of providing a patient positioning apparatus for a neurosurgical intervention, in which an arrangement of the surgical head securing unit on the transfer plate beyond a maximum permissible positioning range is prevented. The object is achieved by the features of the independent claims Advantageous embodiments are described in the sub-claims.

The invention is based on a patient positioning apparatus, comprising a positioning table, a transfer plate, which is arranged on the positioning table so as to be moveable relative to the positioning table, and a positioning unit for positioning a surgical head securing unit on the transfer plate.

It is proposed that the positioning unit exhibits a joint unit with at least one first rotational joint unit, wherein the at least one rotational joint unit exhibits a predetermined stop position for a rotational movement. Preferably, by means of the joint unit, a position of the surgical head securing unit is adjusted in relation to the transfer plate. By way of the embodiment according to the invention, an arrangement of the surgical head securing unit on the transfer plate which projects beyond a maximum permissible positioning range can advantageously be prevented, wherein the maximum permissible positioning range for the surgical head securing unit in this situation is determined and/or delimited by a patient accommodation area of the medical imaging apparatus, for example of a magnetic resonance apparatus. Preferably, the maximum permissible positioning range is formed by a cross-sectional area of the patient accommodation area, less a safety range and/or a tolerance range. Advantageously, in this situation the stop position for a rotational movement is set at the joint unit in such a way that, with an arrangement of the first rotational joint unit in the stop position, the surgical head securing unit is still arranged inside a maximum permissible reclining area for the surgical head securing unit. This accordingly allows for a possible collision to be prevented of the surgical head securing unit and/or the joint unit with the medical imaging apparatus for a medical imaging examination, in particular after the surgical intervention or during an interruption in the surgical intervention, of the patient together with the surgical head securing unit. In addition, a possible collision of the surgical head securing unit and/or the joint unit with the positioning table can also be prevented during a movement of the transfer plate in relation to the positioning table.

In this connection, the expression "transfer plate" should be understood to mean in particular a plate for positioning the patient for a surgical intervention and/or a medical imaging examination of the patient, wherein the plate can be moved between different patient positioning apparatus units, for example between an operating table apparatus and a patient positioning apparatus in order to transport the patient. The surgical head securing unit is preferably formed from a surgical head clamping unit, by means of which the head of the patient is immovably fixed for the surgical intervention.

It is further proposed that the at least one first rotational joint unit exhibits a stop element, wherein the stop element prevents a rotational movement of the at least one first rotational joint unit beyond the predetermined stop position. As a result, an inadvertent and/or automatic over-rotation of the first rotational joint element beyond the predetermined stop position can advantageously be prevented.

Particularly advantageously, the at least one first rotational joint unit is arranged secured to the transfer plate, as a result of which a simple adjustment in terms of design of the stop position for the rotational movement of the at least one first rotational joint unit can be achieved. In particular, in this situation, a change in the stop position for the rotational movement of the at least one first rotational joint unit in relation to the transfer plate can advantageously be prevented. In addition, the stop element can also be positioned particularly simply on the transfer plate and/or at the joint unit.

In an advantageous development of the invention, it is proposed that the joint unit exhibits at least one second rotational joint unit with a second stop position for a rotational movement. By means of the second stop position, a secure arrangement of the surgical head securing unit on the transfer plate can be achieved, and the risk of collision during transportation of the patient positioned on the transfer plate, together with the surgical head securing unit, can be reduced and/or prevented. In addition to this, by means of the second rotational joint unit, a particularly simple positioning of the surgical head securing unit can be achieved.

Particularly advantageously, the second stop position of the at least one second rotational joint unit is dependent on the stop position of the at least one first rotational joint unit. In this situation, a particularly simple adjustment of the two stop positions can be attained, since this can already take place at the adjustment of the first stop position of the first rotational joint unit. If the first rotational joint unit is arranged in the first stop position, then the second rotational joint unit is preferably also located in the second stop position, wherein the second stop position can be dependent on the first stop position alone, and independent of an absolute position of the second rotational joint unit relative to the transfer plate and/or a rotational position and/or an angle of rotation at the second rotational joint unit.

It is further proposed that the joint unit exhibits at least one first limb element, which is arranged between the at least one first rotational joint unit and the at least one second rotational joint unit. In this way it is possible to achieve a particularly advantageous support and/or force transmission between the at least one first rotational joint unit and the at least one second rotational joint unit. It is particularly preferred in this situation that the at least one first limb element is arranged secured to a rotational element of the at least one first rotational joint unit and secured to a rotational element of the at least one second rotational joint unit. Preferably, in this situation the limb element is arranged, with its two end areas arranged along a longitudinal extension, secured in each case to a rotational element of one of the rotational joint units respectively.

An advantageous transfer of a movement of the joint unit onto the surgical head securing unit can be achieved if the joint unit exhibits at least one second limb element, which exhibits one securing element for securing the surgical head securing unit. In addition to this, a simple and rapid positioning of the surgical head securing unit in relation to the transfer plate and/or within a maximum permissible positioning range for the surgical head securing unit can be achieved.

Particularly advantageous in this situation is the fact that at least one second limb element is embodied secured to a rotational element of the at least one second rotational joint unit, such that a direct force transmission from the joint unit onto the surgical head securing unit is made possible. Accordingly, for example, in the event of a rotation of the first rotational joint unit, this movement or force respectively is transferred via the at least one first limb element onto the at least one second rotational joint unit, and via the at least one limb element onto the surgical head securing unit.

An advantageous and simple adjustment of a position of the surgical head securing unit in relation to the transfer plate can be achieved if the at least one first limb element, and that at least one second limb element is embodied secured with different rotational elements of the at least one second rotational joint unit.

In a further embodiment of the invention, it is proposed that the at least one first limb element exhibits a length which corresponds as a maximum to a length of the at least one second limb element. It can be guaranteed in this situation that the second limb element, during a rotational movement of the first rotational joint unit and of the second rotational joint unit, is always arranged inside the maximum permissible accommodation area for the surgical head securing unit. Particularly advantageously, however, the second limb element exhibits a length which is equal to the length of the first limb element.

In a further embodiment of the invention, it is proposed that the joint unit exhibits at least one belt, by means of which a rotational movement of the at least one first rotational joint unit can be transferred to the at least one second rotational joint unit. As a result of this, an advantageous change in the second stop position of the second rotational joint unit as a function of a deflection of the first rotational joint unit from the first stop position can be transferred to the second rotational joint unit. The second stop position is therefore dependent on a deflection angle at the first rotational joint unit, such that maintenance of an arrangement of the surgical head securing unit together with the joint unit can always be achieved within the maximum permissible positioning range for the surgical head securing unit. Preferably, in this situation the at least one first rotational joint unit and/or the at least one second rotational joint unit exhibit in each case at least one rotational element formed by a belt pulley, on which the belt for transferring the rotational movement is mounted. The belt can be formed as a toothed belt and/or a V-belt and/or other belt forms which appear expedient to persons skilled in the art. Preferably, the belt pulleys of the at least one first and/or of the at least one second rotational joint unit are formed by belt pulleys which correspond to the belts, such as, for example, a toothed wheel etc.

Particularly advantageously, the belt is crossed between the first rotational joint unit and the second rotational joint unit, as a result of which the two rotational joint units exhibit different directions of rotation, in particular contrary. In this way, the maximum permissible positioning range for the surgical head securing unit can be exploited to the maximum, without the surgical head securing unit and/or the head of the patient and/or the joint unit thereby leaving the maximum permissible positioning range. In particular, for the second rotational joint unit and, particularly advantageously for the second limb element, the second stop position can always be arranged in a peripheral area of the maximum permissible positioning range. In such a way, a risk can be minimized that a part area of the joint unit leaves the maximum permissible positioning range for the surgical head securing unit during a positioning of the joint unit, in particular during a rotational movement of the rotational joint units. In addition, in this way the risk of collision of the surgical head securing unit and/or of the joint unit with a housing of the medical imaging apparatus during the introduction of the transfer plate, together with the patient, the surgical head securing unit, and the joint unit can be reduced.

It is further proposed that the at least one second rotational joint unit exhibits at least one further rotational element, and the first rotational joint unit exhibits a rotational element, wherein the rotational element of the first rotational joint unit comprises a radius which is twice as large as a radius of the further rotational element of the second rotational joint unit, and a rotational movement can be transferred between the two rotational elements by means of the belt. In this way, an advantageous transfer between the first rotational joint unit and the second rotational joint unit can be achieved, in which, in particular, the second stop position of the second rotational joint unit, in particular of the second limb element, always exhibits essentially the same distance from a limit between the maximum permissible positioning range and an impermissible range. Preferably, the at least one first rotational element and the at least one second rotational element are in each case formed by a belt pulley and/or a toothed wheel, etc.

In an advantageous development of the invention it is proposed that the rotational element of the at least one second rotational joint unit is rotatable in relation to the rotational element, embodied secured to the first limb element, of the at least one second rotational joint unit and/or rotatable in relation to the rotational element, embodied secured to the second limb element, of the at least one second rotational joint unit, wherein the rotatability of the further rotational element in relation to the two rotational elements is limited by the stop position. As a result, a particularly flexible positioning of the surgical head securing unit can be achieved, while maintaining the maximum permissible positioning range.

Particularly reliable maintenance of the maximum permissible positioning range for the surgical head securing unit can be achieved particularly simply if the further rotational element of the at least one further rotational joint unit exhibits a stop element. The stop element is preferably arranged to incur a delimitation of a rotational movement of the rotational element, embodied as secured to the second limb element, in relation to the further rotational element. Alternatively or additionally to this, the rotational element embodied as secured to the second limb element can also exhibit a stop element.

The invention is further based on a medical imaging apparatus with a patient positioning apparatus as claimed in the claims. With this arrangement, particularly advantageously, when a patient positioned on the transfer plate is introduced into the patient examination area of the medical imaging apparatus, such as a magnetic resonance apparatus for instance, a collision between a housing of the medical imaging apparatus and the head of the patient and/or the surgical head securing unit, are advantageously prevented, and the risk of injury to the patient id therefore minimized.

BRIEF DESCRIPTION OF THE DRAWINGS

Further advantages, features, and details of the invention result from the exemplary embodiment described hereinafter and on the basis of the drawings, in which.

DETAILED DESCRIPTION OF INVENTION

Figure 1:
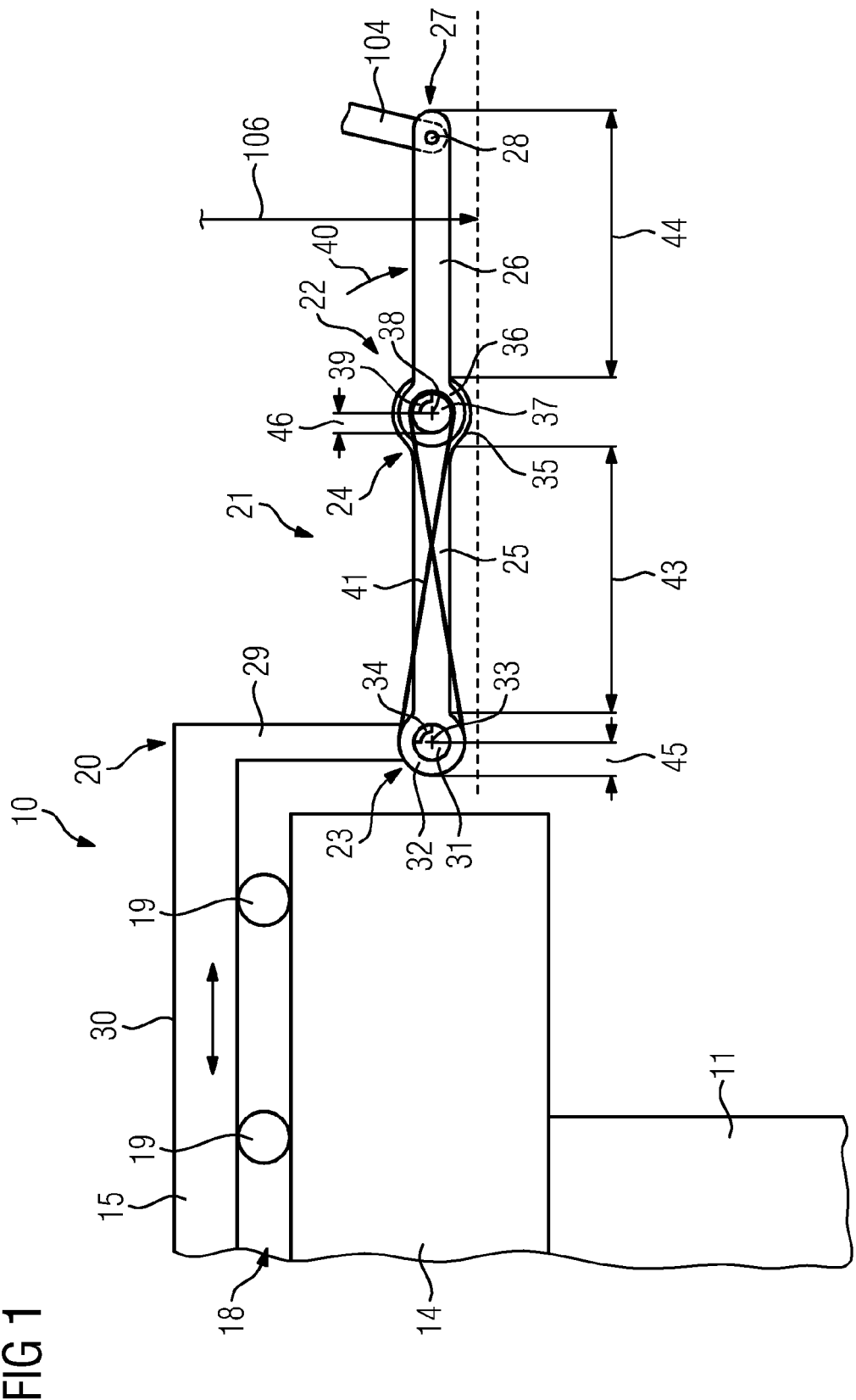
FIG. 1 shows a diagrammatic representation of a part area of a patient positioning apparatus according to the invention, in a first stop position.
Figure 2:
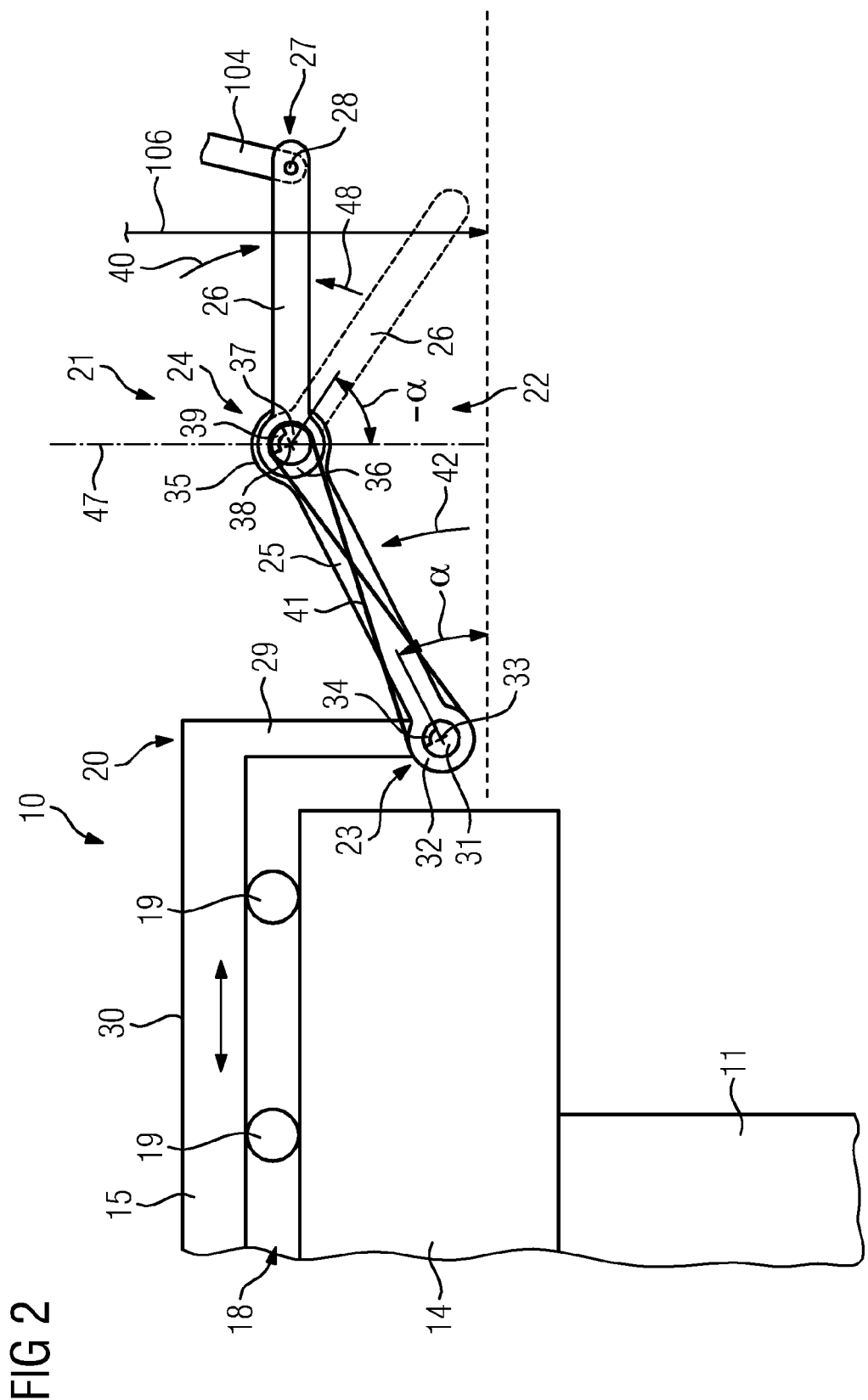
FIG. 2 shows a diagrammatic representation of the part area of the patient positioning apparatus in a further position.

FIGS. 1 and 2 show a diagrammatic side view of a patient positioning apparatus 10 according to the invention. The patient positioning apparatus 10 is formed in this present case by the movable patient positioning apparatus 10, which is designed to transport a patient 100, for example from an operating area to a medical imaging apparatus 101. In addition, the patient positioning apparatus 10 exhibits a coupling unit, not represented in greater detail, for coupling to the medical imaging apparatus 101.

As an alternative to this, the patient positioning apparatus 10 can also be formed from an operating table apparatus, on which the patient 100 is positioned for, in particular, a neurosurgical intervention.

Figure 3:
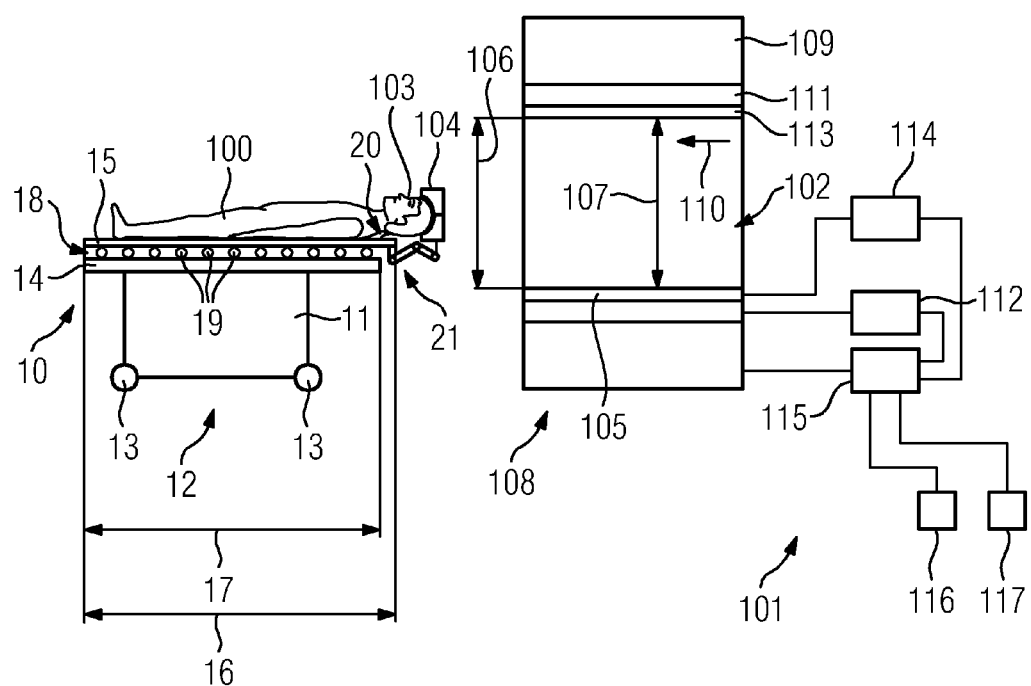
FIG. 3 shows a medical imaging apparatus with the patient positioning apparatus, in a diagrammatic representation.

The patient positioning apparatus 10 exhibits a base unit 11, by means of which the patient positioning apparatus 10 is supported on a floor surface. In order to transport the patient 101, the base unit 11 exhibits forward movement unit 12, with rollers 13, as is represented in FIG. 3. In addition, the patient positioning apparatus 10 exhibits a positioning table 14 and a transfer plate 15. The positioning table 14 is arranged on a side of the base unit 11 facing away from the floor surface. On a side of the positioning table 14 facing away from the base unit 11, the transfer plate 15 is positioned on the positioning table 14, wherein the transfer plate 15 is positioned so as to be movable relative to the positioning table 14 along a longitudinal extension 16 of the transfer plate 15 and/or along a longitudinal extension 17 of the positioning table 14. For this purpose, the patient positioning apparatus 10 further exhibits a slide bearing unit 18, comprising individual slide bearing elements 19, such as, for example, slide rollers, by means of which a low-friction movement or low-friction sliding of the transfer plate 15 in relation to the positioning table 14 is made possible (FIGS. 1 to 3). In this situation, the slide bearing unit 18 is herewith arranged between the positioning table 14 and the transfer plate 15.

Due to the movable positioning of the transfer plate 15 on the positioning table 14, the transfer plate 15 can be moved between different patient positioning apparatuses 10. For example, the patient 100 is positioned on the transfer plate 15, wherein the transfer plate 15 is to this end locked to the positioning table 14 by means of a locking unit, not represented in any greater detail, in particular immovably. For the surgical intervention the patient 100 remains, together with the transfer plate 15, on a patient positioning apparatus 10 designed as an operating table apparatus. In the event of a medical imaging examination being carried out after the termination and/or during an interruption in the surgical intervention, the patient 100, lying on the transfer plate 15, is moved from the operating table apparatus to the patient positioning apparatus 10, designed for a medical imaging examination. This patient positioning apparatus 10 is coupled to the medical imaging apparatus 101, such that the transfer plate 15, together with the patient 100, can be brought into a patient accommodation area 102 of the medical imaging apparatus 101.

For a neurosurgical intervention on the patient 100, the patient 100, in particular the head 103 of the patient 100, is positioned inside a surgical head securing unit 104. The surgical head securing unit 104 comprises a surgical head clamping unit, which is arranged on a front area 20 and/or head area of the transfer plate 15. The surgical head clamping unit projects outwards beyond the front area 20 and/or the head area of the transfer plate 15, such that the head 103 of the patient 100 extends along the longitudinal extension 16 of the transfer plate 15 and projects beyond it.

The surgical clamping unit, together with the head 103 of the patient 100, must in this situation be positioned on the transfer plate 15 in such a way that, at the transfer of the transfer plate 15 and of the patient 100, a collision is prevented between the surgical head clamping element and the positioning table 14 and also with a housing 105 surrounding the patient accommodation area 102 of the medical imaging apparatus 101. In this context, a maximum permissible positioning range 106 is available for the surgical head securing unit 104. This maximum permissible positioning range 106 is determined on the basis of a cross-sectional area 107 of the patient accommodation area 102, less a safety range and/or a tolerance range (FIG. 3).

In order to maintain a position of the surgical head clamping unit within the maximum permissible positioning range 106 during a positioning of the head 103 of the patient 100 inside the surgical head clamping unit, and of the surgical head clamping unit on the transfer plate 15, the patient positioning apparatus 10 further exhibits a positioning unit 21 (FIGS. 1 and 2). The positioning unit 21 is arranged at the front area 20 and/or the head area of the transfer plate 15.

The positioning unit 21 exhibits a joint unit 22 with a first rotational joint unit 23 and a second rotational joint unit 24. As an alternative to this, the joint unit 22 may also comprise more than one first rotational joint unit 23 and also more than one second rotational joint unit 24, such as, for example, with an arrangement of rotational joint units 23, 24, on both sides of the surgical head securing unit 104.

In addition, the positioning unit 21 exhibits a first limb element 25 and a second limb element 26. The first limb element 25 is arranged between the first rotational joint unit 23 and the second rotational joint unit 24, and the second limb element 26 is arranged on the second rotational joint unit 24. At an end area 27 of the second limb element 26, facing away from the second rotational joint unit 24, the second limb element 26 exhibits a securing element 28 for securing the surgical head securing unit 104 at the joint unit 22. The first limb element 25 exhibits a length 43 which is equal to a length 44 of the second limb element 26. Basically, however, it is also conceivable that the second limb element 26 exhibits a length 44 which is smaller than the length 43 of the first limb element 25.

The first rotational joint unit 23 is arranged secured to the transfer plate 15, such that when transporting the patient 100 positioned on the transfer plate 15, together with the surgical head securing element 104, the positioning of the surgical head securing element 104 in relation to the transfer plate 15 is retained. For this purpose, the transfer plate 15 exhibits a securing web 29, on which the first rotational joint unit 23 is securely arranged. The securing web 29 is arranged on a side of the transfer plate 15 facing away from the reclining surface 30 of the transfer plate 15. In addition to this, the first rotational joint unit 23 exhibits at least two rotational elements 31, 32, which can carry out a rotational movement relative to one another about an axis of rotation 33, wherein the axis of rotation 33 is aligned essentially perpendicular to the longitudinal extension 16 of the transfer plate 15, and essentially parallel to the reclining surface 30 of the transfer plate 15. A first of the at least two rotational elements 31 is in this situation arranged secured to the securing web 29. The first limb element 25 is arranged secured to the second rotational element 32 of the first rotational joint unit 23, such that, at a first rotational movement, by means of the first rotational joint unit 23, the first limb element 25 carries out a rotational movement in relation to the securing web 29.

The first rotational joint unit 23 exhibits a predetermined stop position for a rotational movement of the first rotational joint unit 23. In FIG. 1, the first rotational joint unit 23 is represented in this first stop position. In order to maintain the predetermined stop position, the first rotational joint unit 23 exhibits at least one stop element 34, which prevents a rotational movement of the first rotational joint unit 23 beyond the predetermined stop position. In the present exemplary embodiment, the at least one stop element 34 is arranged between the two rotational elements 31, 32 of the first rotational joint unit 23. As an alternative, the stop element 34 can also be arranged on the securing web 29.

The second rotational joint element 34 exhibits at least three rotational elements 35, 36, 37, which are able to carry out a rotational movement about a second axis of rotation 38 in relation to one another. The first limb element 25 is arranged securely on a first rotational element 25 of the second rotational joint unit 24. The second limb element 26 is arranged secured to a second rotational element 36 of the second rotational joint unit 24. In addition to this, the second rotational joint unit 24 likewise exhibits a second stop position for the rotational movement of the second rotational element 36 of the second rotational joint unit 24 in relation to one another, wherein the stop position of the second rotational joint unit 24 is dependent on the stop position of the first rotational joint unit 23.

In order to maintain the second stop position, the second rotational joint unit 24 exhibits a stop element 39, which delimits a rotational movement of the second rotational element 36, and therefore of the second limb element 26, in relation to the third rotational element 37 along a direction of rotation 40, which in the present exemplary embodiment is aligned in the clockwise direction. For this purpose the stop element 40 is preferably arranged on the third rotational element 37 of the second rotational joint unit 24.

In addition, in order to maintain the second stop position, the joint unit 22 exhibits a belt 41, by means of which a rotational movement can be transferred from the first rotational joint unit 23 to the second rotational joint unit 24. The belt 41 can be formed by a V-belt, a flat belt, a toothed belt, and/or further types of belt 41 which appear appropriate to the person skilled in the art. In addition, the second rotational element 32 of the first rotational joint unit 23 and the third rotational element 37 of the second rotational joint unit 24 in each case exhibit a belt pulley corresponding to the belt 41, for example a belt pulley designed for a force transmission by means of a flat belt, and/or a toothed wheel pulley, etc. such that, by means of the belt 41, a rotational movement can be transferred from the second rotational element 32 of the first rotational joint unit 23 onto the third rotational element 37 of the second rotational joint unit 24. The belt 41 is in this situation arranged crossed between the two rotational elements 32, 37, such that the third rotational element 37 of the second rotational joint unit 24, at a rotational movement of the second rotational element 32 of the first rotational joint unit 23, carries out a rotational movement which is opposite to the rotational movement of the second rotational element 32 of the rotational joint unit 32.

The second stop position is therefore dependent on an angle of the second rotational element 32 of the first rotational joint unit 23 in relation to the first rotational element 31 of the first rotational joint unit 23, wherein the angle comprises a change in the deflection from the first stop position into an anti-clockwise direction of rotation 42.

In order to guarantee an arrangement of the second stop position for the second limb element 26 inside the maximum permissible positioning range 106, such that the second limb element 26 is arranged, independently of an angle of rotation of the first limb element 25, inside the maximum permissible positioning range 106, the belt pulley of the second rotational element 32 of the first rotational joint unit 23 exhibits a radius 45, which is twice as large as a radius 46 of the belt pulley of the third rotational element 37 of the second rotational joint unit 24. As a result of this, at a rotational movement of the first rotational joint unit 23, at which the first limb element 25 is rotated by an angle α in relation to the securing web 29, the second stop position of the second limb element 26 is rotated about the angle −α in respect of a parallel axis 47 to the securing web 29 (FIG. 2). Accordingly, the end area 27 of the second limb element 26 facing away from the second rotational element 36 of the second rotational joint unit 24 in the stop position is always arranged inside the maximum permissible positioning range 106, and, specifically, in a critical peripheral area of the maximum permissible positioning range 106.

In the first stop position of the first rotational joint unit 23, the first limb element 25, in particular a longitudinal extension of the first limb element 25, is aligned essentially perpendicular to the longitudinal extension of the securing web 29, wherein the first limb element 25 extends away from the first rotational joint unit 23 along a direction from a foot area of the transfer plate 15 in the direction of the front area 20 and/or head area of the transfer plate 15. In this situation the second rotational joint unit 24 is adjusted in such a manner in relation to the first rotational joint unit 23 that the second limb element 26, in particular a longitudinal extension of the second limb element 26, is likewise aligned essentially perpendicular to the longitudinal extension of the securing web 29 of the transfer plate 15, wherein the second limb element 26 also extends away from the second rotational joint unit 24 along the direction from the foot area of the transfer plate 15 in the direction of the front area 20 and/or the head area of the transfer plate 15. In this situation, the second limb element 26 is in the second stop position.

If the first limb element 25 is not arranged in the stop position of the first rotational joint unit 23, for example after a clockwise rotation of the second rotational element 32 in relation to the first rotational element 31 of the first rotational joint unit 23, then, due to the belt 41, the third rotational element 37 of the second rotational joint unit 24, and therefore also the stop element 39, arranged on the third rotational element 37, is rotated in a counter-clockwise direction (FIG. 2). A maximum deflection and/or rotational movement of the first rotational joint unit 23 is provided in the present exemplary embodiment by the securing web 29 of the transfer plate 15.

The second rotational element 36 of the second rotational joint unit 24, and therefore also the second limb element 26, are mounted such as to be able to rotate in relation to the first rotational element 35 and the third rotational element 37 of the second rotational joint unit 24, wherein a rotational movement in the clockwise direction of the second rotational element 36 of the second rotational joint unit 24 and of the second limb element 26 is limited by the stop element 39 on the third rotational element 37.

From the second stop position (represented in FIG. 2 by the broken line), for a positioning of the surgical head securing unit 104, the second rotational element 36 of the rotational joint unit 24 is rotated counter-clockwise, together with the second limb element 26, along a direction of rotation 48. Preferably, the second rotational joint unit 24 also exhibits a locking element, not represented in greater detail for locking the adjusted position of the second rotational element 36 of the second rotational joint unit 24, together with the second limb element 26.

Represented in diagrammatic form in FIG. 3 is a medical imaging apparatus 101, formed from a magnetic resonance apparatus. The formation of the medical imaging apparatus 101 is not restricted to the present embodiment, however. As an alternative or in addition to this, the medical imaging apparatus 101 may also be formed of a computed tomography apparatus and/or a PET (Positron Emission Tomography) apparatus, etc.

The magnetic resonance apparatus includes a detector unit 108 formed of a magnet unit, with a main magnet 109 to generate a powerful and, in particular, constant main magnetic field 110. In addition, the magnetic resonance apparatus exhibits the cylindrical patient accommodation area 102, to accommodate the patient 100 for the magnetic resonance examination, wherein the patient accommodation area 102 is surrounded in a circumferential direction by the detector unit 108 in cylindrical fashion. The patient 100 can be pushed into the patient accommodation area 102 by means of the patient positioning apparatus 10.

The transfer plate 15 and the positioning unit 21 of the patient positioning apparatus 10 are designed to be magnetic resonance-compatible.

The detector unit 108 further exhibits a gradient coil unit 111 in order to generate magnetic field gradients which are used for spatial encoding during an imaging process. The gradient coil unit 111 is controlled by means of a gradient control unit 112. The detector unit 108 further exhibits a high-frequency antenna unit 113 and a high-frequency antenna control unit 114 for the excitation of a polarization effect, which appears in the main magnetic field 110 generated by the main magnet 109. The high-frequency antenna unit 113 is controlled by the high-frequency antenna control unit 114, and radiates high-frequency magnetic resonance sequences into the patient accommodation area 102.

In order to control the main magnet 109, the gradient control unit 112, and to control the high-frequency antenna control unit 114, the magnetic resonance apparatus exhibits a control unit 115 formed of a computer unit. The control unit 115 controls the magnetic resonance apparatus centrally, such as, for example, carrying out a predetermined imaging gradient echo sequence. Control information, such as imaging parameters for example, and reconstructed magnetic resonance images, can be displayed to an operator on a display unit 116, for example on at least one monitor of the magnetic resonance apparatus. In addition to this, the magnetic resonance apparatus exhibits an input unit 117, by means of which information and/or parameters can be input by an operator during a measurement procedure.

We claim:

1. A patient positioning apparatus, comprising:
   a positioning table; a transfer plate, which is arranged on the positioning table so as to be moveable relative to the positioning table; and
   a positioning unit for a positioning of a surgical head securing unit on the transfer plate,
   wherein the positioning unit exhibits a joint unit with a first rotational joint unit, and
   wherein the first rotational joint unit exhibits a predetermined stop position for a rotational movement, and
   wherein the joint unit exhibits a belt, by means of which a rotational movement of the first rotational joint unit is transferred onto the second rotational joint unit.

2. The patient positioning apparatus as claimed in claim 1, wherein the first rotational joint unit exhibits a stop element, which prevents a rotational movement of the first rotational joint unit beyond the predetermined stop position.

3. The patient positioning apparatus as claimed in claim 1, wherein that the first rotational joint unit is arranged secured to the transfer plate.

4. The patient positioning apparatus as claimed in claim 2, wherein the joint unit exhibits a second rotational joint unit with a second stop position for a rotational movement.

5. The patient positioning apparatus as claimed in claim 4, wherein the second stop position of the second rotational joint unit is dependent on the stop position of the first rotational joint unit.

6. The patient positioning apparatus as claimed in claim 4, wherein the joint unit exhibits a first limb element, which is arranged between the first rotational joint unit and the second rotational joint unit.

7. The patient positioning apparatus as claimed in claim 6, wherein the first limb element is arranged secured to a first rotational element of the first rotational joint unit and secured to a second rotational element of the second rotational joint unit.

8. The patient positioning apparatus as claimed in claim 6, wherein the joint unit exhibits a second limb element, which exhibits a securing element for securing of surgical head securing unit.

9. The patient positioning apparatus as claimed in claim 8, wherein the second limb element is secured to a rotational element of the second rotational joint unit.

10. The patient positioning apparatus as claimed in claim 8, wherein the first limb element and the second limb element are secured to different rotational elements of the second rotational joint unit.

11. The patient positioning apparatus as claimed in 8, wherein the first limb element exhibits a first length which at maximum corresponds to a second length of the second limb element.

12. The patient positioning apparatus as claimed in claim 1, wherein the belt is crossed between the first rotational joint unit and the second rotational joint unit.

13. The patient positioning apparatus as claimed in claim 1,
wherein the second rotational joint unit exhibits a further rotational element, and the first rotational joint unit exhibits a rotational element,
wherein the first rotational element of the first rotational joint unit comprises a first radius, which is twice as large as a second radius of the further rotational element of the second rotational joint unit and a rotational movement is transferred between the two rotational elements by means of the belt.

14. The patient positioning apparatus as claimed in claim 13,
wherein the further rotational element of the second rotational joint unit is rotatable in relation to the first rotational element, embodied secured to the first limb element, of the second rotational joint unit and/or rotatable in relation to the second rotational element, embodied as secured to the second limb element, of the second rotational joint unit, and
wherein the rotatability of the further rotational element in relation to the two rotational elements is limited by the stop position.

15. The patient positioning apparatus as claimed in claim 13, wherein the further rotational element of the second rotational joint unit exhibits a stop element.

16. A medical imaging apparatus, comprising:
a patient positioning apparatus as claimed in claim 1.

* * * * *